(12) United States Patent
Levin et al.

(10) Patent No.: US 6,685,664 B2
(45) Date of Patent: Feb. 3, 2004

(54) METHOD AND APPARATUS FOR ULTRAFILTRATION UTILIZING A LONG PERIPHERAL ACCESS VENOUS CANNULA FOR BLOOD WITHDRAWAL

(75) Inventors: Howard R. Levin, Teaneck, NJ (US); Mark Gelfand, New York, NY (US); Steve Bernard, Yonkers, NY (US)

(73) Assignee: CHF Solutions, Inc., New York, NY (US)

(*) Notice: Subject to any disclaimer, the term of this patent is extended or adjusted under 35 U.S.C. 154(b) by 0 days.

(21) Appl. No.: 09/876,185

(22) Filed: Jun. 8, 2001

(65) Prior Publication Data

US 2002/0187069 A1 Dec. 12, 2002

(51) Int. Cl.[7] .................. A61M 37/00; A61M 1/36; B01D 61/00; B01D 24/00; C02F 1/44
(52) U.S. Cl. .............. 604/5.04; 604/5.01; 604/4.01; 604/6.09; 604/6.16; 604/272; 210/646; 210/650; 210/321.6; 422/44
(58) Field of Search ............ 604/4.01, 5.01–5.04, 604/6.01–6.05, 6.09, 6.11, 6.15–6.16, 8, 27–29, 500, 507–508, 264, 271–272, 523; 422/44; 210/645–647, 650–651, 252, 348, 257.1–257.2, 321.6, 321.71–321.72, 321.74–321.79, 322, 323.1, 323.2; 128/898; 623/3.1, 3.26; 600/433–435

(56) References Cited

U.S. PATENT DOCUMENTS

| | | | |
|---|---|---|---|
| 4,080,958 A | | 3/1978 | Bregman et al. |
| 4,776,841 A | * | 10/1988 | Catalano ............... 604/43 |
| 4,842,582 A | * | 6/1989 | Mahurkar ............... 604/43 |
| 4,906,375 A | * | 3/1990 | Heilmann ............ 210/500.23 |
| 5,120,317 A | | 6/1992 | Luther |
| 5,470,483 A | | 11/1995 | Bene et al. |
| 5,476,451 A | | 12/1995 | Ensminger et al. |
| 5,683,640 A | * | 11/1997 | Miller et al. ............. 264/255 |
| 5,749,835 A | * | 5/1998 | Glantz ................... 600/424 |
| 5,823,961 A | | 10/1998 | Fields et al. |
| 5,837,150 A | | 11/1998 | Langley et al. |
| 5,902,282 A | | 5/1999 | Balbierz |
| 5,910,252 A | * | 6/1999 | Truitt et al. ............. 210/645 |
| 5,928,181 A | * | 7/1999 | Coleman et al. ........... 604/8 |
| 5,989,206 A | | 11/1999 | Prosl et al. |
| 6,059,771 A | | 5/2000 | Balbierz et al. |
| 6,200,287 B1 | * | 3/2001 | Keller et al. ............ 604/6.01 |
| 6,299,575 B1 | | 10/2001 | Bolling |
| 6,387,037 B1 | | 5/2002 | Bolling et al. |
| 6,390,969 B1 | | 5/2002 | Bolling et al. |
| 6,475,186 B1 | * | 11/2002 | Safar et al. ............. 604/101.5 |
| 6,579,259 B2 | * | 6/2003 | Stevens et al. .......... 604/96.01 |
| 2002/0068015 A1 | | 6/2002 | Polaschegg et al. |

FOREIGN PATENT DOCUMENTS

| WO | WO 97/15228 | 5/1997 |
|---|---|---|

OTHER PUBLICATIONS

International Search Report dated Mar. 27, 2003.

(List continued on next page.)

Primary Examiner—Patricia M. Bianco
(74) Attorney, Agent, or Firm—Nixon & Vanderhye, P.C.

(57) ABSTRACT

Method and apparatus for the extracorporeal treatment of blood by utilizing a peripherally inserted catheter assembly for the continuous removal of blood for renal replacement treatment, in particularly, treatment of congestive heart failure and fluid overload by ultrafiltration. A catheter is inserted in a peripheral vein and maneuvered upward through the vascular system to access the reservoir of blood in the large or great veins for continuous blood withdrawal and treatment. Air-tight connectors are incorporated in the catheter assembly to overcome the untoward effects of negative pressure in blood withdrawal.

31 Claims, 5 Drawing Sheets

OTHER PUBLICATIONS

Piergiuseppe Agostoni et al., "Sustained Improvement in Functional Capacity After Removal of Body Fluid With Isolated Ultrafiltration in Chronic Cardiac Insufficiency: Failure of Furosemide to Provide the Same Result", Mar. 1994, The American Journal of Medicine, vol. 96, pp. 191–199.

Daniel Goldstein et al., "Venoarterial Shunting for the Treatment of Right Sided Circulatory Failure After Left Ventricular Assist Device Placement", ASAIO Journal 1997, pp. 171–176.

Michael Berkoben et al., "Hemodialysis Vascular Access", pp. 41–57.

Allan Lauer, "Continuous Arteriovenous Hemofiltration in the Critically Ill Patient", pp. 455–460.

A. L'Abbate et al., "Ultrafiltration: A Rational Treatment for Heart Failure", Cardiology 1989, pp. 384–390.

Yung–Chang Chen et al., "Direct Peripheral Venopuncture: Another New Choice of Temporary Vascular Access", pp. 369–377.

James Cimino et al., "Simple Venipuncture For Hemodialysis", The New England Journal of Medicine, Sep. 20, 1962, pp. 608–609.

Drukker et al., "Replacement of Renal Function by Dialysis", pp. 334–379.

Andrea Rimondini et al., "Hemofiltration as Short–Term Treatment for Refractory Congestive Heart Failure", Jul. 1987, The American Journal of Medicine, vol. 83, pp. 43–48.

Marc Silverstein et al., "Treatment of Severe Fluid Overload by Ultrafiltration", Volumne 291, No. 15, Oct. 10, 1974, pp. 747–751.

* cited by examiner

METHOD AND APPARATUS FOR ULTRAFILTRATION UTILIZING A LONG PERIPHERAL ACCESS VENOUS CANNULA FOR BLOOD WITHDRAWAL

FIELD OF THE INVENTION

This invention relates to the extracorporeal treatment of blood, and more particularly to the blood access for Renal Replacement Therapy or treatments using an artificial kidney. It is also related to the treatment of congestive heart failure and fluid overload in a patient.

BACKGROUND OF THE INVENTION

Renal Replacement Therapy (RRT) is a class of medical treatments that artificially provide functions that would naturally be provided by the kidneys. Mechanical RRT generally involves an extracorporeal blood circuit that treats blood that is temporarily removed from and then returned to a patient. RRT performs two primary functions: (i) ultrafiltration (removal of water from blood plasma), and (ii) solute clearance (removal of different molecular weight substances from blood plasma). Devices used for RRT generally include: an extracorporeal blood circuit that extends from the patient through a filter and back to the patient; a pump acting on the blood circuit tube that moves the blood through the tube and filter, and a filter where the blood components are separated and where the solute exchange takes place. In addition, a RRT device may include a controller to regulate the pumps, which in turn control the flow rate of blood and other fluids through the circuit, and detect blockages and leaks in the blood circuit.

In operation, blood from a patient flows through the RRT blood circuit at a flow rate determined by the pump speed. As the blood flows through the filter, certain fluids, solutes or both from the blood pass through the filter membrane and are extracted from the blood plasma. The extracted fluids with solutes flow from the filter through a filtrate tube and are temporarily stored in a filtrate bag. The extraction of fluids and/or solutes by the RRT device replaces or supplements the natural functions of the kidneys. Fluids may be injected into the remaining blood plasma which then flows through the blood circuit tube and is infused into the patient.

The filter in an RRT device, also called hemofilter or "dialyzer", can be set up to perform fluid removal, solute clearance, or both. The RRT device may also operate with or without fluid replacement. "Clearance" and "ultrafiltration" are common terms used in RRT. "Clearance" is the term used to describe the net removal of substances, both normal and waste product, from the blood. "Ultrafiltration" is the term used to describe the removal of plasma water, without significant affect on the concentration of small solutes in blood plasma, from the blood plasma. In mechanical terms "Ultrafiltration" is the convective transfer of fluid out of the plasma compartment of a filter through pores in the filter membrane and into a filtrate output compartment of the filter.

Blood filters generally have a blood compartment having input and output ports connected to the blood circuit, a filter membrane, and a filtrate compartment. The membrane separates the blood compartment and the filtrate compartment in the filter. In a filter used primarily for ultrafiltration, the pores of the filter membrane may be hollow fibers having blood passages of approximately 0.2 mm or less in diameter. The filter membrane pass fluids, electrolytes and small and middle sized molecules (typically up to 50,000 Daltons) from the blood plasma. The ultrafiltrate output from the filtration pores is similar to plasma, but without the plasma proteins or blood cells. In an ultrafiltration filter, the concentration of small solutes is the same in the ultrafiltrate as in the plasma, and, thus, no clearance or concentration change is obtained of small solutes in the blood plasma that is returned to the patient. However, the ultrafiltration does remove water from the blood and is useful for treating patients suffering from fluid overload. During the ultrafiltration treatment of a fluid overloaded patient the fluid that is mechanically "filtered" or removed from blood is typically immediately replaced by the access fluid that has been stored in the body. As a result the excess fluid or "edema" in the legs, the abdomen and the lungs of the patient is reduced and the patient's condition is relieved.

Dialysis is a different form of RRT. Dialysis is the transfer of small solutes out of a blood plasma compartment of a filter by diffusion across the filter membrane. Dialysis occurs as a result of a concentration gradient across the filter membrane. Diffusion of small solutes occurs from the filter compartment with a higher concentration (typically the blood compartment) to a compartment with lower concentration (typically the dialysate compartment). Since the concentration of solutes in the plasma decreases, clearance is obtained. Fluid removal does not necessarily occur during dialysis.

Ultrafiltration can be combined with dialysis to remove both fluid and small solutes from the blood plasma during RRT. Hemofiltration is the combination of ultrafiltration and fluid replacement. The volume of the replacement fluid is typically much larger than is needed just for fluid control. The replacement fluid generally contains electrolytes, but not other small molecules. There is some clearance because there is a net removal of small solutes due to both replacing fluids without small solutes and ultrafiltration of fluid with small solutes. A primary difference between the ultrafiltration and hemofiltration treatments is that during the former the plasma water removed from blood is replaced by the natural excess fluid internally stored in the patient's body. During the later the replacement solution is supplied by the treatment in a form of an artificial infusion.

Generally, all modes of Renal Replacement Therapy involve the removal of blood (typically venous) from a patient and passing the blood through a hollow fiber filter where there occurs fluid removal and, if desired, a solute removal or exchange. After passing through the filter, the blood is returned to the blood stream of the patient. So-called "batch" type RRT devices extract and return blood through the same single lumen IV catheter or "needle" and blood tube by reversing the direction of the blood pump. More common "continuous" type devices extract and return blood continuously using one double lumen catheter in the same vein or separate catheters in two separate veins. Catheter and needles used in RRT are generally known as "blood access". Some RRT patients have permanently lost their kidney function and need to undergo dialysis several times a week. These patients typically have surgically implanted or modified sited for blood access such as arterial-venous shunts or fistulas.

Another large group of "renal" patients do not have permanent kidney damage. These renal patients have generally healthy kidneys that are not fully functioning, and the kidneys that have allowed the patient to become overloaded with fluids and toxic solutes. These patients require temporary support by an artificial kidney. Some of these patients suffer from Acute Renal Failure (ARF) in which their natural kidneys no longer have the ability to remove excess fluid and toxic solute from their blood stream for days or even weeks. These patients temperately require a RRT that removes both fluids and solutes from the blood stream.

Another large group of patients, who can benefit from fluid removal by ultrafiltration of blood, have functional kidneys, but suffer from fluid overload due to Congestive Heart Failure (CHF). The kidneys of CHF patients are generally healthy but are not fully functioning due to the failing heart and low blood pressure. Because the kidneys are not fully functioning, fluids build up in the patient and the fluid overload contributes to the stress on the already failing heart. However, the kidneys do make some urine that is usually sufficient for the kidneys to remove toxic solutes.

CHF patients need an RRT treatment that removes excess fluid from the body. These patients typically do not require solute removal or a long-term chronic treatment. The fluid can be removed from the patient relatively quickly and the treatment stopped. The reduction of fluid overload should relieve the stress on the heart sufficiently so that the heart is again able to resume adequate perfusion of the kidney. Even if the heart is unable to adequately perfuse the kidney after the fluid overload treatment, the patient often enjoys several days or weeks before the fluid overload condition again becomes sufficiently severe to undergo another ultrafiltration treatment. These CHF patients need an RRT treatment that is simple to establish and safe.

CHF is a condition that occurs when the heart becomes damaged and reduces the blood flow to other organs of the body, including the kidneys. To operate properly, the kidneys require a certain blood flow and perfusion pressure. If the blood flow decreases sufficiently, the kidneys are not adequately perfused and kidney function becomes impaired. Due to the impaired kidney functions, the patient suffers from fluid retention, abnormal hormone secretions and increased constriction of blood vessels. These results from impaired kidney functioning increase the workload of the heart and further decrease the heart's pumping ability. Due to the added work from the poor kidney function, the already-failing heart further reduces the blood flow and pressure. It is believed that the progressively-decreasing perfusion of the kidney is a principal non-cardiac cause perpetuating the downward spiral of the "Vicious Cycle of CHF". Moreover, the fluid overload and associated clinical symptoms resulting from these physiologic changes are the predominant cause for excessive hospital admissions, terrible quality of life and overwhelming costs to the health care system due to CHF.

Fluid overload can lead to several painful and dangerous conditions, including excessive fluids in the lungs. If excessive fluid in the lungs is not promptly removed with a diuretic medication, CHF patients are often intubated and placed on a ventilator. If the initial diuretic therapy has little affect, more aggressive treatment with increasingly potent diuretics is needed. In addition, inotropic agents such as dobutamine are administered to increase the pumping function of the heart and raise the blood pressure. Higher blood pressure is expected to assist in the perfusion of the kidneys and make diuretics work. In more recent years, vasodilator therapy became a part of the standard therapy for a severely volume-overloaded, decompensated CHF patient. All the above-mentioned therapies as a rule require admission to an intensive care unit (ICU) of a hospital. Potentially dangerous side affects of drugs and the need for advanced monitoring and intubation are the main reasons for a typical ICU admission. However, ICU admissions are expensive and require specialized doctor and nurse caregivers.

The primary causes of admission in CHF patients are symptoms of severe shortness of breath from fluid overload in the lungs. Symptoms of fluid overload are excessive fluid retained in the abdomen, legs and lungs. Of these, fluid in the lungs is the most dangerous and can cause patients to have difficulty breathing. Fluid or "edema" in the lungs leads to poor blood oxygenation. Poor oxygenation leads to acidosis and deleterious neurological and hormonal phenomena that increases vasoconstriction and load on the heart. In addition, vasoconstriction leads to reduced blood flow to the kidneys and diminishes the effectiveness of the main pharmacological means of fluid removal—diuretic treatment. This phenomenon is known as the "vicious cycle" of CHF heart failure. Accordingly, there is a need for a simple and effective treatment to quickly relieve fluid overload and particularly to remove excessive fluid from the lungs.

Previously, standard drug therapy was frequently unable to remove excess fluid rapidly enough to prevent hospitalization. There is a clear and unmet clinical need for a CHF treatment that allows physicians to rapidly, controllably and safely remove a clinically significant amount of fluid from a CHF patient. Such a treatment would potentially reduce the need for excessive hospital admissions and decrease the duration of hospital stays.

Ultrafiltration (one mode of Renal Replacement Therapy) is useful for removal of excess fluid from a patient, especially in CHF patients whose kidneys are not working but are generally healthy. Ultrafiltration has not been used widely in the treatment of patients with CHF, despite its clinical benefits for treating fluid overload. There are several issues that have in the past limited the use of currently available ultrafiltration devices. One of these factors is that prior ultrafiltration devices draw large blood volumes of blood out of the body and, thus, require so called central venous access. Central venous access implies that a relatively large diameter catheter is placed with its tip in a major vein in the "center" of the patient's body. Typically the central catheter is placed in the superior vena cava or right atrium of the heart of the patient. To place the catheter, a physician makes a percutaneous tunnel under fluoroscopic guidance into an internal jugular vein, external jugular vein or a subclavian vein. The right internal jugular vein is the preferred insertion site. This approach offers a curved route to the superior vena cava. The catheter tip should reside at the junction of the superior vena cava and right atrium or in the right atrium to ensure a high blood-flow rate. This just-described procedure requires high skill. It is also associated with serious complications such as bleeding, perforated lung or heart and infections. As a result, mechanical fluid removal in CHF patients has in the past been used in the ICU of a hospital where resources, training and adequate nursing monitoring are available.

With the increasing prevalence of decompensated CHF and the increased cost of hospital admission and even more so of an ICU treatment, a strong need has emerged for a new technology that will allow fluid removal in the non critical care setting. This need is for a device and technique that is simple and safe so that it could be used in the outpatient setting, doctor's offices, Emergency Rooms (ER) and general hospital floors. Such treatment would be acceptable if access to venous blood was established via a peripheral vein in the patient's arm or other peripheral vascular site on the patient. An advantage of accessing blood through a peripheral vein in the arm is well recognized. Unlike the central veins, the peripheral veins are close to skin and easy to identify. Physicians and nurses are trained to place needles and catheters in the peripheral veins of an arm. Venopunctures are easy to monitor for infiltration of fluid and thrombosis and the control of infection is simpler than with central catheters. Also, potential loss of a peripheral vein to thrombosis is less critical.

SUMMARY OF THE INVENTION

Recently, applicants invented an ultrafiltration technique that relies on peripheral vein access. This ultrafiltration technique is described in commonly-owned U.S. Pat. No. 6,533,747 and entitled "Extracorporeal Circuit for Peripheral Vein Fluid Removal", the entirety of which is incorporated by reference, and in (now pending U.S. patent application Ser. No. 09/618,759, filed Jul. 18, 2000) and entitled "Method and Apparatus for Peripheral Vein Fluid Removal in Heart Failure", the entirety of which is incorporated by reference. The volume of blood that can be drawn from a peripheral vein is substantially less than can be drawn from a central access vein. Nevertheless, the relatively-small volume of blood removed from peripheral veins has been found sufficient for ultrafiltration for most CHF patients suffering from fluid overload.

Clinical trials of ultrafiltration in CHF patients have been performed using standard and novel devices for peripheral access to blood. Ultrafiltration using peripheral vein access with standard needles or catheters has recently successfully treated several CHF patients. However, standard peripheral vein access has not been successful for all CHF patients. The peripheral vein access had been performed using conventional short (3–4 cm long) catheters inserted into a peripheral vein in the arm of the patient. The peripheral veins in some CHF patients have such poor blood flow that the veins collapse around the area of the catheter tip when short peripheral catheters were used to continuously draw blood for ultrafiltration. For these patients, the blood in the peripheral veins available for withdrawal is not a sufficient for ultrafiltration. These CHF patients require some other blood withdrawal mechanism to remove fluids from their blood stream and provide relief from fluid overload. Accordingly, there is a need for ultrafiltration devices for patients having poor blood flow through their peripheral veins that is inexpensive, relatively easy to apply and does not require a hospital ICU.

There is a need for a simplified removal of excess fluid from fluid overloaded patients that have poor blood flow in their peripheral veins. For those patients having poor blood flow in peripheral veins, devices and methods have been developed and are disclosed here to remove excess fluids through extended length blood access catheters introduced via a peripheral vein, for example, in the patient's arm. These devices and methods safely continuously withdraw blood from a peripheral vein at substantially higher flow rates than the peripheral vein would normally permit. The volume of blood withdrawn from the venous system of a patient through a catheter inserted into a peripheral vein is sufficient for ultrafiltration and fluid overload relief, even for those patients having poor blood flow in their peripheral veins. These devices and methods are safer and simpler than the traditional central vein access catheters.

In forty percent (40%) to eighty percent (80%) of relatively young and healthy people with good veins, continuous blood flow of 40 to 120 mL/min (milliliters per minute) can be established via standard short length (3–4 cm) peripheral vein access needles or catheters. Peripheral veins in the arm such as basilic, cephalic or antibrachial vein are often used to infuse medication or to draw blood from a patient. Patients are commonly asked to increase their blood supply to the arm by squeezing a rubber ball to improve the blood withdrawal. This method using short length catheters is commonly used in extracorporeal blood treatment procedures such as aphaeresis. When patients and blood donors do not have appropriately large veins, they are usually not accepted for treatment. Where the treatment is lifesaving, such as in chemotherapy for blood cancer, central line catheters are placed to allow access to blood.

Based on clinical studies, peripheral vein access using short length catheters has had limited success for blood withdrawal to perform fluid removal in chronically ill CHF patients. Many CHF patients have poor blood flow through their peripheral veins. Effective fluid removal treatment for CHF patients generally requires fluid removal rate of 250 to 1000 mL/Hour. It has been discovered that the 500 mL/Hour fluid removal rate is preferred by physicians in CHF patients.

It is not practical to extract more than 20% to 30% of volume of blood as ultrafiltrate. This implies that to remove 500 mL/Hour (8.3 mL/min) of fluid from the patient, continuous blood flow of at least 40 mL/min through the filter is desired. Attaining this rate in many CHF patients can be difficult. CHF patients are typically elderly. The surface veins in the arms of many CHF patients have been punctured many times during prior medical treatments, and the veins often have stenosis. Moreover, as a result of heart failure, these patients have reduced cardiac output (i.e., total amount of blood pumped by the heart). In response to their poor cardiac output, the circulatory system of these patients reduces the blood supply to peripheral organs (including the arms and the hands), in order to maintain an adequate blood supply to the brain, heart and other vital organs.

Applicants determined that the difficulties with withdrawing blood at rates of 40 to 60 mL/min were due primarily to two conditions:

(a) Intermittent collapse of the peripheral vein around the tip of the withdrawal catheter needle. The vein collapse appears to have been due (at least in part) to the small caliber of the surface peripheral veins used for withdrawal and low venous pressure in the vein. Suction of blood at the tip of the catheter generated a negative pressure zone in the blood and caused intermittent vein collapse. The collapse of the vein prevents withdrawal of blood until the vein returned to its original shape. This first condition could be compensated for in some CHF patients by straightening or relaxing the arm of the patient.

(b) Flow demand determined by the pump in the ultrafiltration device exceeded the blood supply available to the peripheral vein being used for withdrawal. Because the pump demanded a flow of blood more than was available in the peripheral vein, a negative pressure resulted that collapsed the vein. While the pump controller had automatic feedback that reduced the pump speed when the pressure in the withdrawal tube began to drop, the feedback controller could not adequately compensate for the inadequate blood flow through the peripheral vein in some CHF patients.

Based on experiments, it was concluded that a fundamental problem of blood withdrawal from a peripheral vein is the dependence on the drainage from the arm and the hand for blood supply. The available blood flow for withdrawal in a surface peripheral vein is limited to the blood draining from the capillary system. If the blood draining from the capillary system is not sufficient for ultrafiltration treatment, then using conventional local peripheral vein access to withdraw blood becomes unworkable. This problem of inadequate drainage of blood from the capillary system is greatly exacerbated in CHF patients where the arterial blood supply to the arm is reduced compared to healthy subjects.

A solution to inadequate blood flow for withdrawal from peripheral veins is to withdraw blood from other regions of the circulatory system that have a generous supply of blood flow. For example, central catheters draw blood from the large pool of venous blood in the right atrium or the adjacent vena cava. Venous blood collected in these "great vessels" is the combined drainage from all body organs. Even in a CHF patient with reduced cardiac output it is never less than 3 to 4 L/min. The caliber of these central vessels is large compared to the size of the catheter and continuous withdrawal of as much as 200 to 400 mL/min is possible, even for CHF patients.

Central venous catheters have been used to perform Renal Replacement Therapy and fluid removal in CHF patients. However, central venous catheters are difficult to inserting into a patient, require surgery and fluoroscopy to be inserted and removed and generally are closely monitored while a patient is in an ICU during the entire ultrafiltration treatment. Moreover, the risk associated with the placement of central venous catheters limit their use to critically ill patients. Central venous catheters are generally inserted as a life saving measure to relieve critically dangerous fluid overload conditions in CHF patients in danger of imminent death.

The inventive devices and methods disclosed here provide a means for relieving fluid overload in CHF patients who cannot be successfully treated with the conventional peripheral vein blood withdrawal but in whom the placement of central catheters is not desired or justified. The devices and methods developed by applicants combine the access to a large pool of blood (an advantage of central catheters) with the ease and safety of the peripheral vein access. By combining the advantages of central catheter access and peripheral vein access, the present invention provides a technique for providing ultrafiltration (or other RRT treatment such as slow continuous hemofiltration at modest replacement rates) for those patients that have inadequate blood flow in their peripheral veins outside of the ICU environment.

Theoretically, all veins in the human body are connected. The network of veins in a human body include a trunk vessel (central venous cavity) connected to the right atrium of the heart. From the central venous cavity extends many branches of veins that each branch progressively to smaller and smaller veins until the veins become tiny capillaries that connect to the arterial circulatory system. In the venous system, blood drains from the capillaries and flows to the progressively larger veins until all veins drain into the large flow of the central venous cavity. Thus, the largest supply of blood in the venous system is downstream of the blood flow, which is ultimately the central venous cavity. In contrast, the largest supply of blood in the arterial system is upstream because blood flows from the central arteries and downstream towards the capillaries.

In the venous system, it would be useful to draw blood from the downstream sources of venous blood. However, to draw blood from downstream of the peripheral vein from the location near the insertion point of a catheter would require that blood flow backward from the central venous pool through the network of branching vessels into the catheter. Drawing venous blood from downstream in a vein is a technique known as retrograde (opposite to the natural direction) flow. In contrast to retrograde flow, antegrade flow is the withdrawal of blood in the same direction as the natural flow of blood.

Retrograde blood withdrawal from the peripheral vein in an arm (or other body extremity) where these veins come to the body surface and where the traditional catheters are inserted is almost impossible because the peripheral veins in arms and legs prevent retrograde flow and do not allow for blood to flow upstream to a catheter tip intake opening. Peripheral veins have a series of one-way valves (venous flapper valves) along their path. These one-way valves prevent retrograde flow, and prevent venous blood from the central venous cavity flowing upstream through the vein towards the catheter tip. The valves are spaced along the length of the peripheral vessels. The valves are constructed of flappers or leaves that can be bent easily in the downstream direction to permit the downstream flow of blood. The flappers shut closed if the flow of blood reverses and this closure prevents the upstream (retrograde) flow of blood through peripheral veins.

The natural purpose of venous flapper valves is to prevent retrograde blood flow when a person moves and thereby applies inertia and centrifugal forces to the blood in the veins. The valves also prevent pooling of blood at the lower extremities, e.g., hands and feet, due to the force of gravity. In patients that have defective "incompetent" venous valves, it is common to see bulging distended veins in the legs. These venous valves, which appear to work quite well in some CHF patients, prevent retrograde flow of blood to a short peripheral catheter inserted into the arm of a CHF patient. It is believed that the venous flappers are a principal reason why retrograde flow is prevented when a peripheral catheter applies a local negative pressure in a peripheral vein. Accordingly, there is a need to overcome or circumvent the natural venous flappers. By circumventing these flappers, a peripherally inserted catheter should be able to create a sufficient negative pressure to cause retrograde blood flow and, thus, increase the blood flow through a catheter for ultrafiltration treatment without collapsing the vein.

BRIEF DESCRIPTION OF THE DRAWINGS

A best mode embodiment of the invention is illustrated in the attached drawings that are described as follows.

DETAILED DESCRIPTION OF EMBODIMENT DISCLOSED IN THE DRAWINGS

Figure 1:
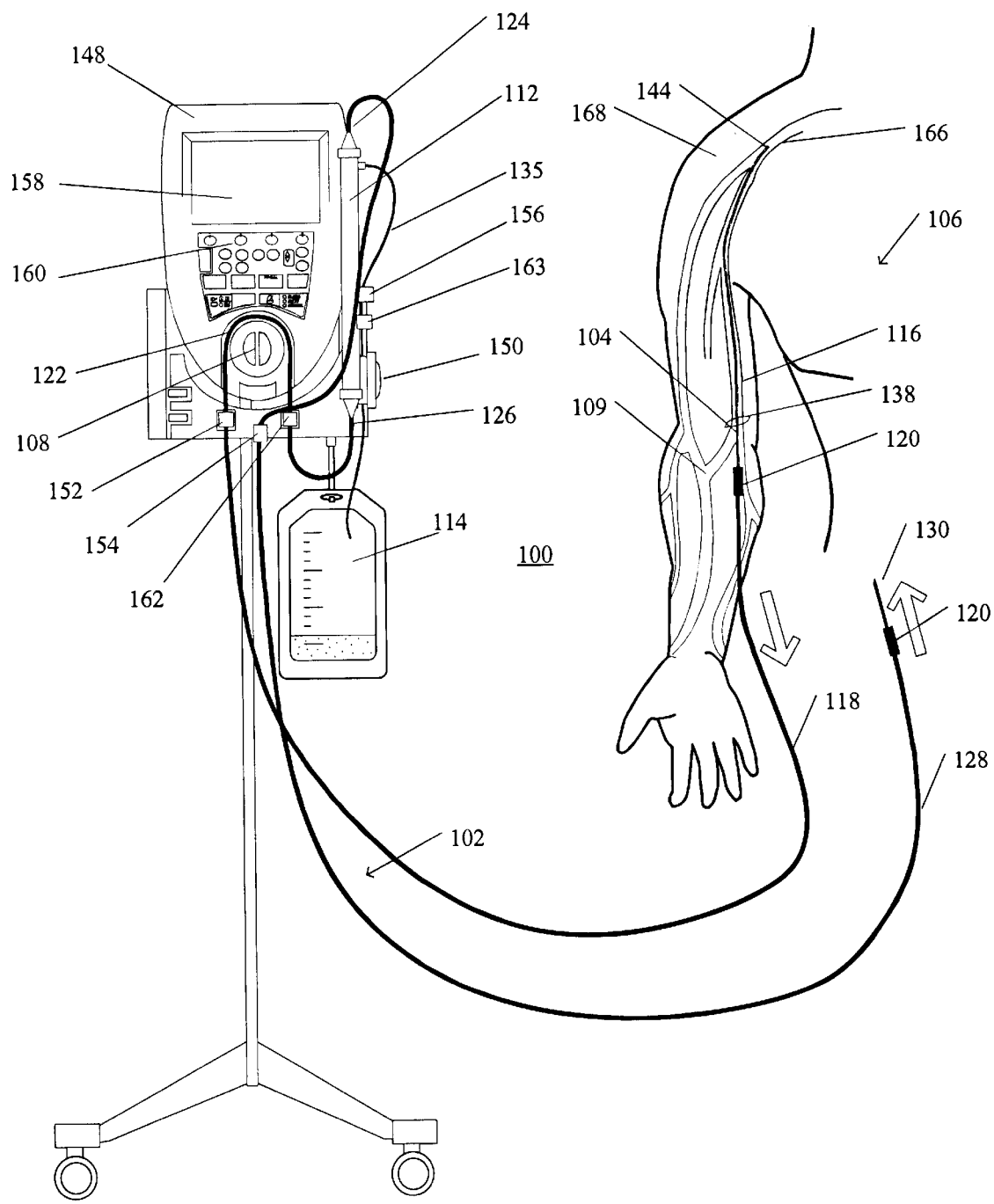
FIG. 1 is a perspective view of an intravenous blood ultrafiltration system using a middle length peripheral access venous blood withdrawal catheter.

FIG. 1 shows an intravenous blood ultrafiltration system 100 having an extracorporeal blood circuit 102 that includes a middle length peripheral access venous blood withdrawal cannula 104, commonly called a Peripherally Inserted Central Catheter (PICC). The disclosed blood circuit is a single use disposable set for ultrafiltration of blood to treat fluid-overload in patients 106. The ultrafiltration system and blood circuit are intended to be used in a non-ICU setting and to not require surgery.

Effective treatment of fluid overload by ultrafiltration of blood generally requires 40 or more mL/min of withdrawn blood. The rate of blood flow required for ultrafiltration would consume substantially all of the blood flowing through the peripheral veins of many CHF patients. However, only a portion of the blood flowing through the peripheral vein may be withdrawn. During blood withdrawal, the resistance of interconnecting branches of the venous tree 109 slows the refilling of a specific vein segment and further reduces the rate of blood flowing through the peripheral vein and available for peripheral withdrawal.

Figure 2:
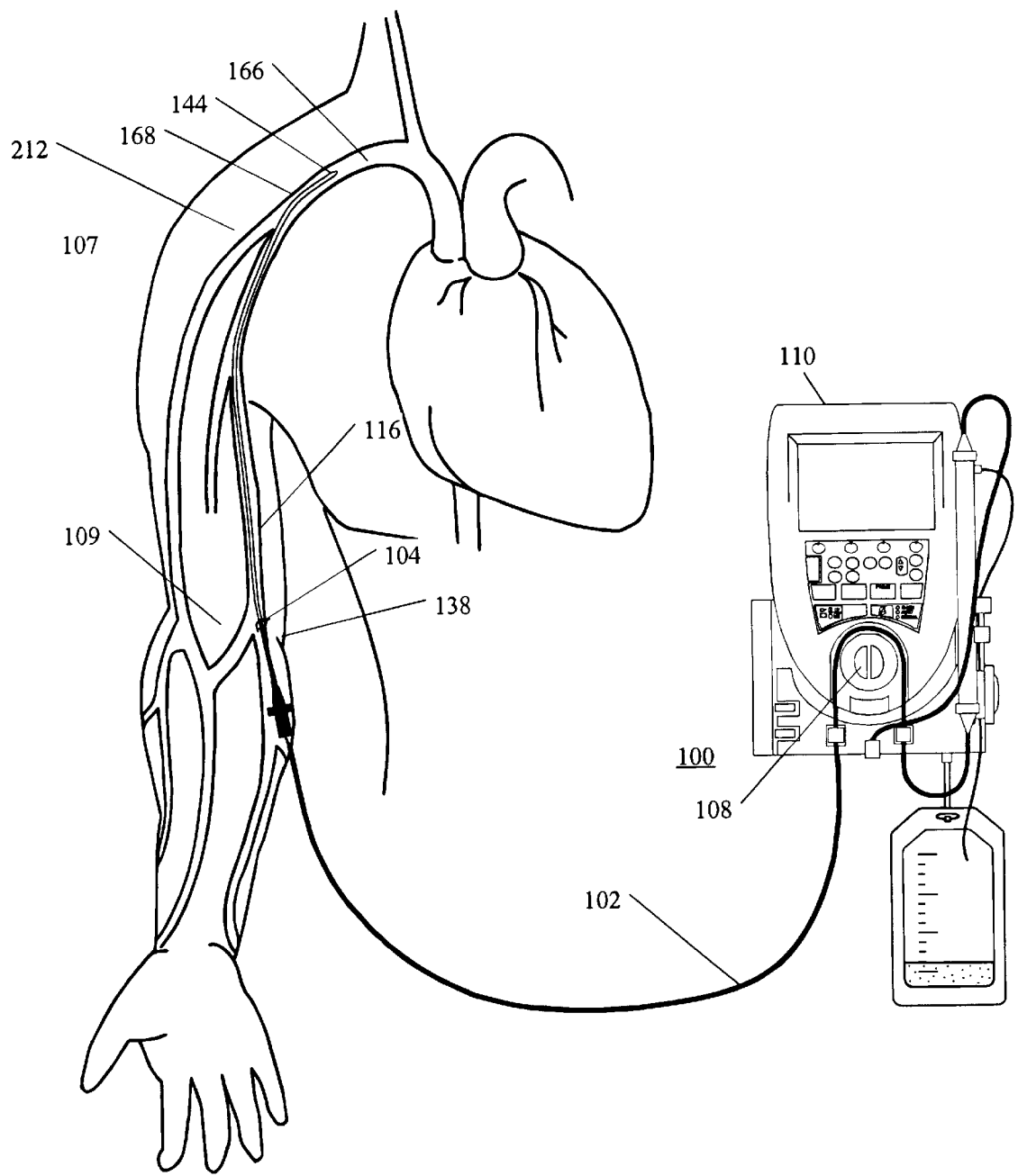
FIG. 2 illustrates the placement of the peripheral access venous blood withdrawal catheter in the patient.

With reference to FIG. 2, the maximum flow rate of venous blood that can be withdrawn from the peripheral vein 116 (such as in the arm 109 of the patient) in the proximity to the catheter insertion location 138 is the rate of blood that returns (drains) from the network of skin and muscle blood capillaries. These capillaries are supplied by oxygen rich arterial blood coming from the left ventricle of the heart. Moreover, the total venous drainage from an organ cannot exceed the arterial blood supply to the organ. An arm and a hand in a healthy person at rest have a blood supply rate of approximately 100 to 260 mL/min of blood. This rate can very with the hand temperature. In a heart failure patient the flow rate in the arm and hand can be reduced by 20% to 40% below the rate of a healthy person. Accordingly, the flow rate of blood through a peripheral vein in a CHF patient may be only 50 to 208 mL/min.

In addition, the caliber of peripheral veins 116 in the arm in a person can be 2 to 3 mm. A metal or plastic 16 to 20 Gage phlebotomy needle is commonly used to draw blood for various clinical needs. A standard catheter needle for a peripheral vein phlebotomy can be 25 to 45 mm long. If a 16 Gage needle (approximately 1.65 mm outer diameter) is placed in such a vein it will almost occlude the vein and will be prone to collapse the walls of the vein around it with the application of negative pressure. Also, blood vessels in an arm tend to vasoconstrict (contract) in response to neurological and hormonal stimuli. The patient's motion can intermittently cut off the blood supply.

For effective ultrafiltration treatment to relieve fluid overload, blood should be removed from a CHF patient at a rate of 40 to 100 mL/hour. At these rates, four (4) to twelve (12) hours of peripheral vein access ultrafiltration will result in the removal of two (2) to four liters (4) of filtrate fluid from the blood. Generally, 2 to 4 liters of fluids are removed to relieve a CHF patient suffering fluid overload. A treatment time of 4 to 12 hours is relatively long and often there is a strong desire to complete the treatment in a period closer to 4 hours. Increasing the blood withdrawal flow rate is a key to minimizing the ultrafiltration treatment time. It has been difficult to increase the withdrawal flow rate, especially in those CHF patients having low blood flow through their peripheral veins. Conventional techniques for increasing blood flow are not practical. For example, it is not practical to expect that a heart failure patient in a severe fluid overload condition will squeeze a rubber ball in his hand to improve blood flow to the arm for 4 to 12 hours. Accordingly, there is a need for devices and techniques to withdraw blood from peripheral veins at substantially higher rates than have in the past been obtainable.

In view of the limitations described above, fluid removal in volume overloaded CHF patients via a peripheral vein using standard-length phlebotomy needles has been impractical for many CHF patients. Experiments have been conducted for blood withdrawal and infusion using 20 Gage, 18 Gage and 16 Gage plastic needles 35 to 40 mm long inserted in lateral antibrachial, cephalic, basilic and other adjacent surface veins at the arm bend at the elbow of patients. These patients varied widely in body size, age and medical condition. The objective of the experiment was to withdraw blood continuously using a computer controlled roller pump at 40 to 60 mL/min. Blood was continuously re-infused into a different vein in the opposite arm of the patient. During the experiment, treatment time ranged from 15 minutes to 4 hours. Infusion of 40 to 60 mL/min of blood into almost any vein in the arm or hand of CHF patients was always possible. However, withdrawal of blood from peripheral veins at the same rates of 40 to 60 mL/min was problematic in as many as 50% of CHF patents and impossible in as many as 20% of these patients.

Blood can be withdrawn from a large volume 166 of venous blood that is upstream of the peripheral veins at the large and great veins of the vascular system. A wide variety of Peripherally Inserted Central Catheters (PICC) 104 exist for clinical medical practice. A typical PICC is approximately 35 to 65 cm long (or as short as 20 to 25 cm), and between 0.5 and 1.75 mm outside diameter. PICCs are used to infuse a medication when the long term continuous infusion or repeated frequent infusions are desired. PICC catheters are often left in place for weeks and months.

PICCs generally have one or two internal lumens. The external surface of a PICC is usually marked with gradations allowing the user to gage the length of insertion. PICCs are made of silicone, polyurethane or other medical plastics. They are flexible so as to follow the path of a tortuous vein, but stiff enough to resist kinking when inserted into a vein. Prior to insertion of a PICC, the medical practitioner measures the distance from the site of insertion to the point 168 on the body surface that approximately corresponds to the location where the tip 144 of the catheter is desired. The catheter length is trimmed to correspond to the distance between the catheter insertion point 138 on the skin and the desired tip location. The total tube length (i.e., the distance in the catheter traveled by the blood) for the catheter is generally no greater than 75 cm so as to avoid excessive flow resistance to the blood.

The medical practitioner inserts the catheter using a common medical technique, such as an "over the wire" method or through a hollow introducer needle that is later pealed apart and removed. If access to the right atrium is desired, the length of a typical PICC is 65 cm. If the catheter tip is positioned in a basilic, auxiliary or cephalic vein at the level or just below the shoulder 212, it is often called a "mid-line" catheter and extends approximately 25 cm into the arm venous system.

It is not uncommon to place the tip 144 of the catheter in the subclavian vein in between the two lengths described above. Thus, PICC catheters can be inserted into peripheral veins at the elbow bend such that the tip of the catheter is beyond the venous flappers in the extremities of the vein. PICCs are typically used for infusion of medicine and infrequently for the withdrawal of small amounts of blood for blood tests. PICC catheters that extend to the level of the shoulder or beyond have not been connected to blood pumps for the withdrawal of a continuous flow of blood or for purposes of Renal Replacement Therapy and particularly fluid removal by ultrafiltration.

A catheter similar to a common PICC may be used for the continuous withdrawal of blood for ultrafiltration. The rate of blood that can be withdrawn using a PICC catheter is sufficient to provide for clinically significant amount of ultrafiltration and provide relief to patients suffering from fluid overload. A PICC has sufficient length such that it extends beyond the venous flappers that would block retrograde flow. The length of the PICC can be selected by the medical practitioner so as to extend from the insertion point on the patient's arm, along the peripheral vein to a point near the shoulder where the peripheral vein no longer has venous flappers.

Figure 3:
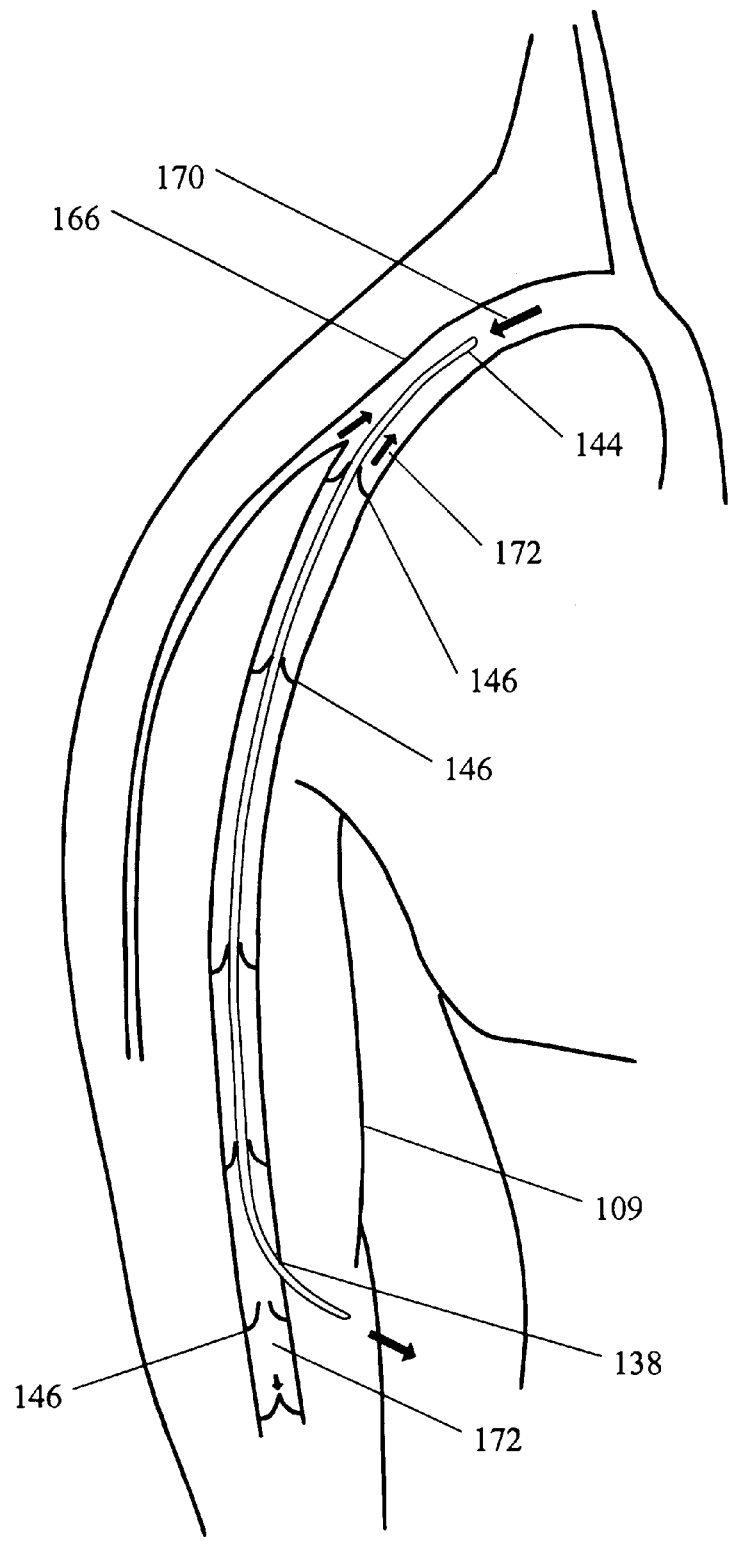
FIG. 3 is an illustration of transverse section of a peripheral vein showing an open and closed valve.

The PICC catheter 104 may be connected to an extracorporeal blood circuit 102 (FIG. 1) for ultrafiltration or other RRT treatment. The blood circuit may include a blood pump 108 that moves blood through the circuit and applies a considerable (−100 to −300 mmHg) negative pressure to a PICC catheter. Most of this negative pressure serves to overcome the hydraulic resistance of the PICC tube to blood flow. The slight negative pressure at the tip of the PICC catheter causes retrograde flow 170 (FIG. 3) at the catheter tip, if the downstream blood flow 172 (antegrade) is insufficient. The retrograde flow supplements the antegrade flow so that there is a sufficient flow of withdrawn blood into the PICC and maintains sufficient pressure in the vein to prevent collapse.

The retrograde flow in the vein draws blood through the vein from the central body venous blood supply, such as in the vena cava and other larger veins. By drawing blood using retrograde flow, the PICC 104 provides blood to the extracorporeal circuit at a rate greater than the rate that could be withdrawn using antegrade flow alone, that is a limitation of conventional methods using short phlebotomy needles. Accordingly, a PICC catheter has the double benefit of the safety, ease and comfort of peripheral vein access, and the high withdrawal flow rate available when using retrograde venous flows.

Moreover, a PICC extends the benefits of mechanical fluid removal by eliminating certain risks that previously limited its use. A PICC catheter 104 is inserted through a peripheral vein 109 in the patient's arm, in a manner only slightly more complex than the insertion of a common phlebotomy or IV medication needle. When inserted, the tip of the PICC catheter resides in a larger venous vessel 166. Such larger venous vessels may be just below the shoulder, in the shoulder or in a subclavian vein slightly above the shoulder. Even access to the vena cava or right atrium of the heart is not out of reach of certain long PICC catheters. Thus, the advantages of the retrograde blood flow, impossible with common catheter needles, become accessible using a PICC catheter.

The flapper valves 146 in peripheral veins do not generally extend beyond the shoulder of a person. By extending the tip of a PICC catheter beyond the last venous flapper valve in a vein, there is no longer a natural barrier separating the tip of the PICC catheter from a large supply of central blood 166. The blood withdrawal via a PICC catheter is not limited to the antegrade blood flow from venous drainage from capillaries in the hand and arm. Rather, the tip of the PICC catheter can draw blood from substantially the entire cardiac output of the patient. This large supply of available blood at the tip of a PICC catheter should be sufficient for the operation of the extracorporeal apparatus. Already, PICC catheters have been used by inventors in clinical trials to successfully relief fluid from CHF patients that could not be successfully treated using a standard withdrawal catheter.

Unlike conventional central venous catheters, PICCs can be inserted by non-surgeons. The process of inserting a PICC catheter is only slightly more complicated and requires only a bit more skill than does the placement of a standard catheter. However, non-surgical doctors, many skilled nurses and skilled physician assistants are or can be trained to insert PICC catheters. In modern hospitals thousands of nurses are currently trained to place PICC catheters.

Moreover, PICC catheters may be inserted in emergency rooms, in clinics and in many other locations where there are medical persons trained to insert PICC catheters. Once the PICC catheter is inserted, the patient may rest comfortably in a bed or chair while blood is withdrawn. The extracorporeal blood circuit and associated device, such as an ultrafiltration device, need not be particularly large or complex. The blood circuit and device may be positioned on a stand next to the patient. The device may also be sufficiently automated so that it may be operated by most medical personnel (that are familiar with the operation of the device) and does not require constant operator attention.

The patient can sit or lie comfortably during the ultrafiltration, RRT or other blood treatment. During treatment, the patient may relax watching television or reading a book; talk to others in the room or by telephone, conduct light personnel or business work, such as computer or telephone operation, or do other light tasks normally done while sitting. Because there is only a small PICC withdrawal catheter and a return catheter inserted in a peripheral vein, the patient may be able to stand and move about a bit for comfort during treatment. In addition, the PICC catheter may remain in the patient between blood treatments (if the patient will have to have several treatments during the course of a few weeks).

PICC catheters have not previously been used to continuously withdraw blood for Renal Replacement Therapy, blood donation or aphaeresis. In addition, PICC catheters have not been used to circumvent the venous flappers or provide a large supply of withdrawn blood by creating retrograde flow. PICC catheters have not previously been used for continuous blood withdrawal and the other features for which they are used in the present application because PICC catheters have been considered too small. The largest PICCs are five (5) French size, which has an external diameter of 1.7 mm (millimeters). To ensure that the catheter is flexible and does not kink, PICC catheters have conventionally had a small internal lumen (no more than 1.0 or 1.1 mm in diameter). PICCs have a small internal diameter and a long passage. This combination of features in a flow passage results in a high flow resistance to fluids, such as blood, in the catheter. Thus, it has been considered impractical to draw blood through a long PICC catheter for continuous extracorporeal blood treatment. Indeed, it was believed that to overcome the flow resistance in a PICC catheter an extreme negative pressure would have to be applied to the inlet of the PICC catheter.

Moreover, the traditional designers of blood pumps and circuits for fluid removal targeted primarily the treatment of renal failure, such as dialysis or hemofiltration. These therapies require blood flow in the range of 100 to 400 mL/min to be effective. These high blood flow rates are exceedingly difficult to draw through a PICC catheter. A low pressure (or large negative pressure) must be applied to the inlet of the PICC catheter to draw blood through that catheter. A low pump inlet pressure is needed to apply the low PICC inlet pressure and this low pump inlet pressure is a main limitation for blood withdrawal through a small gage long catheter, e.g., a PICC catheter.

A low inlet blood circuit pressure to a pump is problematic. Roller pumps, that are typically used for extracorporeal pumping of blood, lose accuracy of calibration when operated at pressures below −200 (negative 200) mmHg (millimeters of mercury). In addition, the conventional wisdom has been that blood, when subjected to negative pressures, will release gases normally contained in solution and that these gases will create bubbles.

Further, the connectors used for conventional PICC catheters and conventional blood circuits are all standard so called "luer" connectors. Luer connectors were designed (and adopted as a standard) initially to connect syringes and IV needles for injections. Initially all such connectors were made of glass and steel and could be manufactured with great precision. Luer connectors have cone shaped coupling male and female parts that, if precision ground, engage and seal very tightly. Lately many medical devices and particularly IV needles became disposable. Cost constrains made it necessary to mold needle hubs, syringes and luer connectors from plastic. This is particularly true in regard to extracorporeal blood circulation circuits, where cost is important and reuse is highly undesirable. Molded inexpensive plastic parts cannot be manufactured with the same degree of precision as their steel and glass predecessors.

Modern plastic luer connectors are easy to use, inexpensive and resist sufficiently to the positive pressure inside. Even if small leaks develop in a luer connector under positive pressure owing to poor fit, such leaks usually are not dangerous, easy to identify and can be corrected or tolerated. Luer and Luer lock (ones that can be secured) connectors are not intended to and do not withstand significant negative pressure. When subjected to negative pressures, lure lock connectors frequently leak air bubbles into the blood circuit. Even small amount of air, if infused into a patient, can be dangerous and cannot be tolerated. Since inventors wanted to withdraw blood through a high resistance PICC catheter, standard luer connectors of blood catheters to catheters had to be abandoned in favor of the design that can withstand negative pressure. Similar to traditional ones, the special airtight connectors were made from plastic using inexpensive injection molding technique. Unlike luer connectors, they do not rely on a tight fit of cone shaped male and female parts to establish the seal. Connectors use the silicone rubber gasket as a seal between the coupled parts of the connector. When the connector is engaged and locked, the seal is compressed. This way the quality of seal is not dependent on the precision of tolerances used in manufacturing of plastic parts.

Connectors using compression gaskets are well known and used in different industrial and commercial applications. Inventors used connectors designed and manufactured with Colder Products Company (St. Paul, Minn.). Such connectors were never used previously as a part of a blood access device to connect extracorporeal circuits to catheters for blood treatment. Consequentially there have never been PICC catheters with hubs adapted to connect to such devices. Inventors developed a novel PICC with an airtight connector specifically designed for safe blood withdrawal.

Applicants have conceived and actually reduced to practice a blood circuit having a PICC catheter that overcome the traditional problems associated with continuous blood withdrawal through PICC catheters. Applicants have demonstrated that PICC catheters and similar long catheters can be effectively and beneficially used to continuously withdrawal blood at rates sufficient for effective treatments, such as the removal of excess fluid in CHF patients. For example, a removal rate of excess fluid in a range of 250 to 750 mL/hr (or even in a range of 0.1 to 1.0 liters per hour) would be appropriate to treat CHF patients. To achieve this excess fluid removal rate, the blood flow through the filter may be no greater than 40–60 milliliters per minute which is about two percent of the total cardiac output of the patient. Applicants discovered that some of the dangers perceived with PICC catheters do not occur under the conditions associated with blood withdrawal for ultrafiltration. For example, a blood pump need only apply a negative pressure of 150 to 200 mmHg to draw blood through the PICC catheter. Blood gas bubbles occur at pressures of negative 500 mmHg, and lower.

In addition, applicants focused on treatments that could be successfully performed using the relatively low blood rates that can be achieved through a PICC. For example, ultrafiltration to relieve patients suffering form fluid overload requires blood flow rates of at least 40 mL/min. A blood flow rate of 40 mL/min can be achieved with the blood having hematocrit (volume fraction of red blood cells in blood) of 40%, through the PICC that is 35 cm long with a 1.1 mm internal diameter lumen. The PICC catheter internal diameter may be in a range of 0.9 to 1.2 mm. Under those conditions, a pressure drop of 180 mmHg across the PICC catheter should draw 40 mL/min of blood through the catheter. In addition to the pressure drop needed across the PICC catheter, the total negative pressure needed at the inlet of the pump depends on the pressure drop between the pump and the PICC catheter due to gravity and the resistance of blood circuit tube from the PICC catheter to the pump. A negative pump pressure of minus 250 mmHg is a reasonable estimate of the pressure needed to achieve a 180 mmHg pressure differential across the PICC catheter.

The ultrafiltration system and PICC may be used to treat fluid overload in a CHF patient 106 (FIG. 1). In particular, the exemplary system described here is an ultrafiltration apparatus designed for the extraction of plasma water (ultrafiltrate) from human blood. The system may be equally applicable to extraction of ultrafiltrate from the blood of mammalian animals other than humans. Moreover, the system may also be adapted to blood treatments other than ultrafiltration and to treatments that are in addition to ultrafiltration, such as the addition of drugs, solutions of electrolytes or other material to the blood.

To extract plasma water, the ultrafiltration system includes a blood pump 108, a pump controller 110, and an extracorporeal blood circuit 102. The blood circuit is connected to the blood pump. The pump forces blood through a blood passage in the circuit. Another pump 150 may be used to move filtrate from a filter 112 in the circuit to a filtrate bag 114. The blood passage includes a withdrawal catheter 104 that is inserted into a peripheral vein 116 near the skin surface of an extremity of the patient, such as an arm. The withdrawal catheter is connected to a withdrawal blood circuit tube 118 via an airtight connector 120. The withdrawal tube may loop through a roller drive 122 of a roller pump 108. The end of the withdrawal tube is connected to a blood input port 124 of the filter 112. The filter has a blood output port 126 that is connected to an end of an infusion blood circuit tube 128. An opposite end of the infusion tube may be connected to an infusion catheter 130 via an airtight connector 120. The infusion catheter may be inserted into the same arm that has the withdrawal catheter. Moreover, the infusion catheter may be inserted into the same or a different peripheral vein as is inserted the withdrawal catheter. In addition, the infusion catheter may be a short catheter and need not be a PICC catheter.

Figure 4:
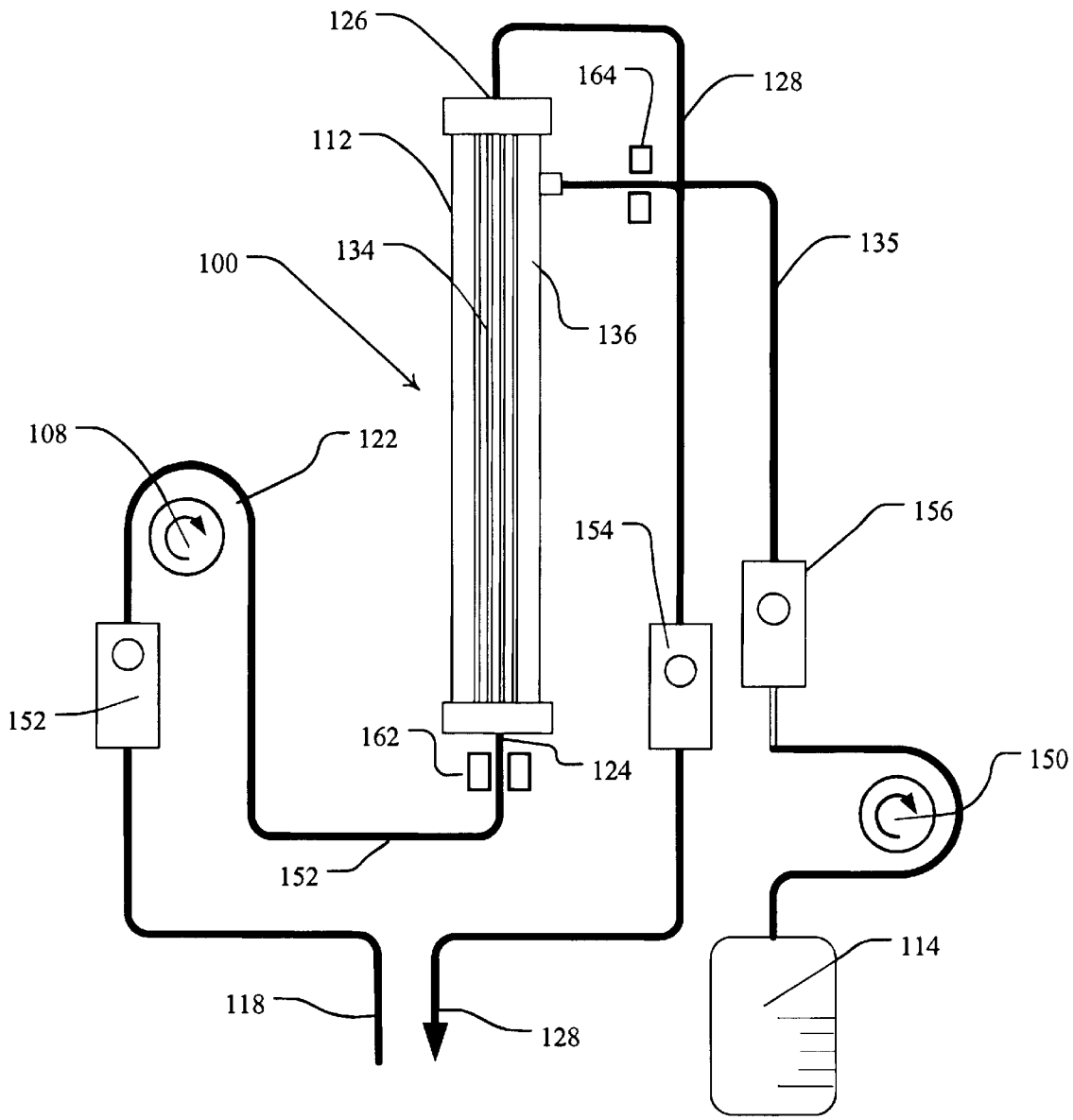
FIG. 4 is a schematic diagram showing a fluid path of blood and removed fluids for the blood circuit used with the blood ultrafiltration system shown in FIG. 1.

The filter 112 includes a blood compartment 134 (FIG. 4) having the blood inlet port 124 and the blood outlet port 126. The blood compartment is separated by a filter membrane 134 from a filtrate compartment 136 of the filter. The filter membrane is permeable to water and small molecules. The membrane is impermeable to blood cells, proteins and other large solutes particles. The patient 106, such as a human or other mammal, may be treated while in bed or sitting in a chair and may be conscious or asleep. The PICC withdrawal catheter 104 and return catheter 130 may be attached to the patient in a hospital, doctor's office or an outpatient clinic (provided that adequate supervision of a doctor or other medically trained person is present).

To initiate ultrafiltration treatment, a withdrawal cannula 104 for withdrawing blood is introduced into a suitable peripheral vein 116 in the patient's arm 138 using an introducer needle (not shown), a guide wire (not shown) and other standard accessories using one of available and well-known medical techniques for introducing and localizing a peripherally inserted central catheter. For example, a guide wire may initially be inserted into a peripheral vein 116 in the arm of a patient and then slid through the vein by a skilled nurse, doctor or other train medical professional until the tip 144 of the PICC extends into one of an auxiliary vein, a subclavian vein, a vena cava, and a right atrium of the heart and beyond the last venous flapper 146. The location of the last venous flapper may be estimated by measuring, prior to insertion of the catheter, the distance on the surface patient's arm from the PICC insertion point to a location just below the shoulder, which will be past the last flapper. The PICC can be cut or marked prior to insertion to indicate when it is been inserted far enough up the vein to extend beyond the last venous flapper.

If the insertion of the PICC into the right atrium is desired, placement of the catheter is usually confirmed by an X-ray. This is done because the wrong placement can result in the catheter tip being in the jugular vein (draining blood from the brain) of the patient. If a more common placement in the auxiliary or the subclavian vein is desired, confirmation of placement is not necessary. Properly-measured length of the catheter is sufficient to ensure that the catheter is not in a position where it can be dangerous to the patient. Operator can draw a small amount of blood from the catheter using a syringe to ensure that the catheter is not kinked or placed in a dead-end in a small brunch vessel. The same length measurement typically ensures that the catheter is above the level of last flapper valve that does not typically extend beyond the shoulder. If when the blood pump is started, the computer controls of the pump indicate to the operator that the blood flow is insufficient, the catheter can be carefully advanced several centimeters further into the vein to pass the valve.

An infusion (return) needle 130 is introduced into a suitable peripheral vein (on the same or different arm) for the return of the blood. This procedure of inserting a needle cannula uses standard gauge size needles and is similar to that used for inserting catheter needles to withdraw blood or for intravenous (IV) therapy. The needles are attached to withdrawal tubing 118 and return tubing 128, respectively. The tubing may be secured to skin with adhesive tape.

As shown in FIG. 1, the ultrafiltration apparatus 100 includes a blood pump console 148 and a blood circuit 102. The console includes a rotating roller blood pump 108 and a filtrate pump 150 that move blood and ultrafiltrate fluids through the circuit, respectively, and the circuit is mounted on the console. The blood circuit (detailed in FIG. 4) includes a continuous blood passage between the withdrawal cannula 104 and the return cannula 130. The blood circuit includes a blood filter 112; pressure sensors 152 (in withdrawal tube), 154 (in return tube) and 156 (in filtrate output tube); an ultrafiltrate collection bag 114 and tubing catheters to connect these components and form a continuous blood passage from the withdrawal to the infusion catheters an ultrafiltrate passage from the filter to the ultrafiltrate bag. The blood passage through the circuit is preferably continuous, smooth and free of stagnate blood pools and air/blood interfaces. The circuit may come in a sterile package and is intended that each circuit be used for a single treatment.

The extracorporeal blood circuit 102 mounts on the console and, in particular, the blood pump 108 (for blood passage) and filtrate pump 150 (for filtrate output of filter). The circuit can be mounted, primed and prepared for operation within minutes by one operator. The operator of the blood ultrafiltration apparatus, e.g., a nurse or medical technician, sets the maximum rate at which fluid is to be removed from the blood of the patient. These settings are entered into the blood pump console 148 using the user interface, which may include a display 158 and control panel 160 with control keys for entering maximum flow rate and other controller settings. Information to assist the user in priming, setup and operation is displayed on the LCD (liquid crystal display).

The ultrafiltrate is withdrawn by the ultrafiltrate pump 150 into a graduated filtrate collection bag 114. When the bag is full, ultrafiltration stops until the bag is emptied. The controller may determine when the bag is filled by calculating the amount of filtrate entering the bag based on the volume displacement of the ultrafiltrate pump in the filtrate tube and filtrate pump speed, or by receiving a signal indicative of the weight of the collection bag. As the blood is pumped through the circuit, an air detector 162 monitors for the presence of air in the blood circuit. A blood leak detector 164 in the ultrafiltrate output monitors for the presence of red blood cells in the ultrafiltrate. Signals from the air detector and/or blood leak detector may be transmitted to the controller, which in turn issues an alarm if a blood leak or air is detected in the ultrafiltrate or in the blood tubing of the extracorporeal circuit.

Regardless of the RRT modality desired, the basic principles of the apparatus design that are relevant to this invention remain the same. Blood that is withdrawn from the patient flows into the withdrawal tubing 118 and enters the blood passage of the blood circuit and is monitored by pressure sensor 152. Blood passes through the hollow membrane fibers 134 of the filter 112, and is returned to the patient via the return tube 128. Ultrafiltrate, effluent or dialysis solution passes through the filter casing surrounding the blood filled hollow fibers. These fibers have blood passages of approximately 0.2 mm. The walls of each fibers are porous, but retain blood solutes greater than 50,000 Daltons. Prior to return, blood passes through the pressure sensor 156 in the infusion tube. Pump 108 generates and controls the flow of blood, using the pressure sensor signals as a feedback signal. Pump 150 generates and controls the flow of ultrafiltrate. The ultrafiltrate tube 135 has a pressure sensor 156 that provides a feedback signal to the filtrate pump 150.

From the blood pump 108 to the filter 112, blood traverses through an air detector sensor 162 that will cause the pump to stop if air is detected in the blood circuit. An air bubble indicates a leak or break in the blood circuit. An air bubble can be dangerous if passed into the bloodstream of the patient. Accordingly, the detection of an air bubble will cause an alarm and stop the pumps. The blood leak detector 163 is a photometric device that uses infrared light beam to detect presence of red blood cells in the ultrafiltrate. The detection of blood in the ultrafiltrate tube indicates a filter failure because blood cells should not normally pass through the filter membrane into the filtrate tube.

The blood and ultrafiltrate pressure sensors 152, 154, and 156 are included in the disposable cartridge and are intended for one-time use. Air detector and blood leak detector are mounted on the system console and have means to clamp around the plastic tubing that forms the fluid passage.

Figure 5:
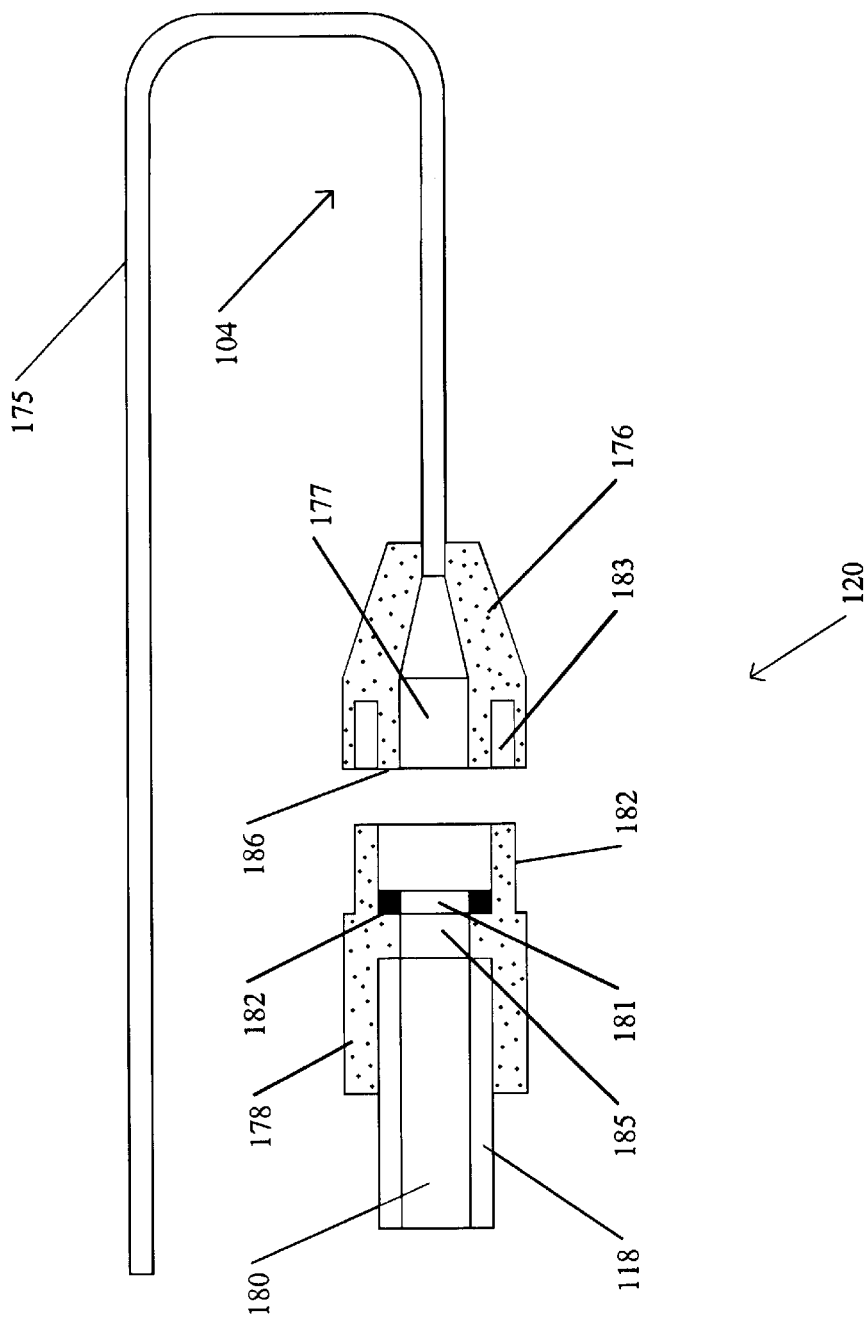
FIG. 5 is an illustration of a middle length peripherally inserted catheter with an airtight connector.

FIG. 5 shows a simplified drawing of the extended length peripherally inserted catheter for blood withdrawal 104 and the airtight connector 120. Catheter tubing 175 is insertion molded into the plastic hub 176. The internal cavity of the tube 175 is in fluid communication with the internal cavity 177 of the hub. A concentric groove 183 in the hub 176 forms the female part of the coupling 120 when engaged with the concentric male portion of the blood tubing part of the connector 178. Blood tubing 118 is inserted and bonded into the tube connector 178. A compression ring seal 181 resides on the internal shoulder 184 of the tubing connector. When the connector assembly is coupled the concentric protruding male part 182 is inside the concentric groove 183 and provides alignment. A face 186 of the catheter hub compresses the seal 181 against the shoulder 184. A locking mechanism (not shown) prevents the seal from disengaging. The internal blood filled cavity of the tubing 180, cavity of the tubing connector 185 and cavity of the catheter hub 177 forms a continuous smooth blood filled passage with the internal surface or the ring 181. This continuous blood filled passage prevents turbulence and clotting of blood. The compressed seal 181 prevents ingress of air into the blood when negative pressure is present inside the blood filled cavity.

Although the present invention has been described in terms of a particular embodiment, it is not intended that the invention be limited to that embodiment. Modifications of the disclosed embodiment within the spirit of the invention will be apparent to those skilled in the art. The scope of the present invention is defined by the claims that follow.

What is claimed is:

1. A method of withdrawal and return of blood in a patient undergoing extracorporeal blood treatment therapy comprising:
    a. inserting a blood withdrawal catheter into a surface peripheral vein in the patient's arm;
    b. advancing the catheter into a venous tree of the patient towards the heart a distance in a range of 20 to 65 cm and positioning a distal tip of the catheter beyond venous flappers in the peripheral vein, wherein the advancement ceases to position the tip in a vein at a shoulder of the patient;
    c. continuously drawing blood from the catheter;
    d. applying an extracorporeal treatment to the blood, and
    e. returning the treated blood to the patient.

2. A method as in 1 where the treatment is ultrafiltration and the catheter is positioned in the vein for a period of at least four hours.

3. A method as in 1 where the treatment is hemofiltration and the catheter is positioned in the vein for a period of at least four hours.

4. A method as in 1 where the treatment is dialysis and the catheter is positioned in the vein for a period of at least four hours.

5. A method as in 1 where the treatment is selected from a group consisting of collecting platelet, collecting peripheral blood stem cells and performing a therapeutic apheresis procedure.

6. A method of extracorporeal circulation of blood for medical therapy treatment therapy comprising:
    a. inserting a blood withdrawal catheter into a surface peripheral vein in an arm of a patient;
    b. advancing the catheter into a venous tree of the patient and towards a heart until the catheter tip and ceasing the advancement when a distal tip of the catheter reaches beyond venous flappers and reaches one of an auxiliary vein, subclavian vein or vena cava;
    c. drawing blood from the tip of the catheter;
    d. applying extracorporeal treatment to the blood, and
    e. returning the treated blood to the patient.

7. A method as in claim 6 where the catheter is inserted a length a range of 20 to 65 cm into the peripheral vein and venous tree.

8. A method as in claim 6 where the insertion of the catheter is at the elbow level of the arm.

9. A method as in claim 6 wherein the catheter has an outside diameter in a range of 1.0 to 1.75 mm.

10. A method as in claim 6 wherein the catheter has a total tube length no greater than 75 cm.

11. A method as in claim 6 wherein the catheter has a catheter lumen internal diameter in a range of 0.9 to and including 1.2 mm.

12. A method of continuous extracorporeal circulation of blood for medical treatment therapy comprising:
    a. inserting a blood withdrawal catheter into a surface peripheral vein in an extremity of the patient;
    b. advancing the catheter into a venous tree of the patient and towards a heart of the patient until a catheter tip has substantially passed venous valves in the venous tree and ceasing the advance when a catheter tip reaches one of an auxiliary vein, subclavian vein or vena cava;
    c. withdrawing blood from the tip of a catheter in a retrograde flow direction;
    d. applying extracorporeal treatment to the withdrawn blood;
    e. returning blood to the patient.

13. A method as in claim 12, where substantial negative pressure is applied to the catheter to overcome resistance of the catheter to blood flow.

14. A method as in claim 12 where the extracorporeal treatment step further comprises:
    e. coupling a blood withdrawal tube to the catheter and to a filter, and passing withdrawn blood through the filter to separate excess fluid from the blood.

15. A method as in claim 14 wherein a blood flow through the filter is less than two percent of a total cardiac output of the patient, and a flow of the excess fluid removed from the blood is at a rate up to and including 1.0 liters per hour.

16. A method as in claim 12 wherein the reduced pressure draws blood from the reservoir of blood upstream through the vein into the withdrawal catheter.

17. A method as in claim 12 wherein the blood withdrawal catheter is a peripherally inserted central catheter (PICC).

18. A method as in claim 17 wherein the PICC catheter is at least 25 centimeters long.

19. A method as in claim 12, wherein a rate of the removal of blood is no greater or equal than 40 milliliters per minute.

20. A method as in claim 12, wherein a rate of the removal of blood is in a range of 40 to 60 milliliters per minute, and a rate of removal of the excess fluid is at a rate of up to and including 1.0 liters per hour.

21. A method as in claim 12, wherein the surface peripheral blood vessel is a basilic vein.

22. A method as in claim 12, wherein the surface peripheral blood vessel is a cephalic vein.

23. A method as in claim 12, wherein the filtration is ultrafiltration.

24. A method as in claim 23, wherein the extracorporeal treatment is to pass the withdrawn blood through a filter to remove fluids from the blood.

25. A method as in claim 24, wherein the filter includes capillary hollow fibers have filtering pores which retain in the blood solutes greater than 50,000 Daltons.

26. A method as in claim 24, wherein the hollow fibers have blood passages of approximately 0.2 mm or less in diameter.

27. A method as in claim 24, wherein blood flows continuously through the filter during periods when a blood pump is reducing pressure on the withdrawal catheter.

28. An extracorporeal method for treating blood from a patient comprising:
   a. withdrawing blood through a withdrawal needle in a surface peripheral vein in an extremity of the patient, and determining that an amount of blood being withdrawn is insufficient for treating the blood;
   b. replacing the needle with a blood withdrawal catheter inserted in the surface peripheral vein, and maneuvering the catheter through the vein to position a tip of the catheter in one of a large vein, great vein or vena cava to access a reservoir of blood for continuous blood withdrawal;
   c. continuously drawing blood from the reservoir of blood into the withdrawal catheter and into a withdrawal blood tube of an extracorporeal blood circuit, and
   d. applying a suction pressure to the withdrawal blood tube to cause blood to flow into the blood withdrawal catheter, and
   wherein the treatment is ultrafiltration and the catheter is positioned in the vein for a period of at least four hours.

29. A method for treating blood from a patient comprising:
   a. withdrawing blood through a withdrawal needle in a surface peripheral vein in an extremity of the patient, and determining that an amount of blood being withdrawn is insufficient for treating the blood;
   b. replacing the needle with a blood withdrawal catheter inserted in the surface peripheral vein, and maneuvering the catheter through the vein to position a tip of the catheter in one of a large vein, great vein or vena cava to access a reservoir of blood for continuous blood withdrawal;
   c. continuously drawing blood from the reservoir of blood into the withdrawal catheter and into a withdrawal blood tube of an extracorporeal blood circuit, and
   d. applying a suction pressure to the withdrawal blood tube to cause blood to flow into the blood withdrawal catheter, and
   where the treatment is hemofiltration and the catheter is positioned in the vein for a period of at least four hours.

30. A method for treating blood from a patient comprising:
   a. withdrawing blood through a withdrawal needle in a surface peripheral vein in an extremity of the patient, and determining that an amount of blood being withdrawn is insufficient for treating the blood;
   b. replacing the needle with a blood withdrawal catheter inserted in the surface peripheral vein, and maneuvering the catheter through the vein to position a tip of the catheter in one of a large vein, great vein or vena cava to access a reservoir of blood for continuous blood withdrawal;
   c. continuously drawing blood from the reservoir of blood into the withdrawal catheter and into a withdrawal blood tube of an extracorporeal blood circuit, and
   d. applying a suction pressure to the withdrawal blood tube to cause blood to flow into the blood withdrawal catheter, and
   wherein the treatment is dialysis and the catheter is positioned in the vein for a period of at least four hours.

31. A method for treating blood from a patient comprising:
   a. withdrawing blood through a withdrawal needle in a surface peripheral vein in an extremity of the patient, and determining that an amount of blood being withdrawn is insufficient for treating the blood;
   b. replacing the needle with a blood withdrawal catheter inserted in the surface peripheral vein, and maneuvering the catheter through the vein to position a tip of the catheter in one of a large vein, great vein or vena cava to access a reservoir of blood for continuous blood withdrawal;
   c. continuously drawing blood from the reservoir of blood into the withdrawal catheter and into a withdrawal blood tube of an extracorporeal blood circuit, and
   d. applying a suction pressure to the withdrawal blood tube to cause blood to flow into the blood withdrawal catheter, and
   wherein the treatment is ultrafiltration.

* * * * *